United States Patent [19]

Lefebvre

[11] Patent Number: 4,990,156
[45] Date of Patent: Feb. 5, 1991

[54] FILTER FOR MEDICAL USE

[76] Inventor: Jean-Marie Lefebvre, 219, boulevard de la Liberté, 59800 Lille, France

[21] Appl. No.: 365,970

[22] Filed: Jun. 14, 1989

[30] Foreign Application Priority Data

Jun. 21, 1988 [FR] France .................. 88 08689

[51] Int. Cl.$^5$ ............................. A61M 25/04
[52] U.S. Cl. ..................... 606/200; 606/191
[58] Field of Search .............. 606/191, 194, 195, 198, 606/200; 604/104

[56] References Cited

U.S. PATENT DOCUMENTS

| | | | |
|---|---|---|---|
| 3,540,431 | 11/1970 | Mobin-Uddin | 606/200 X |
| 4,425,908 | 1/1984 | Simon | 606/200 X |
| 4,643,184 | 2/1987 | Mobin-Uddin | 606/200 |
| 4,727,873 | 3/1988 | Mobin-Uddin | 606/200 |
| 4,793,348 | 12/1988 | Palmaz | 606/194 |
| 4,817,600 | 4/1989 | Herms et al. | 606/200 |

Primary Examiner—Robert A. Hafer
Assistant Examiner—Kevin G. Rooney
Attorney, Agent, or Firm—Shenier & O'Connor

[57] ABSTRACT

A medical filter and catheter for positioning and using the filter, which filter is particularly intended to be implanted in a blood vessel such as the inferior vena cava through the endovenous route via a catheter. The filter has a filtering section which opens out in the vessel when it is in position in the patient and which has no hooks for engaging the vessel wall. The filter has a holding section which holds the filter section in position in the vessel and which facilitates transition from a temporary use of the filter to definitive use.

16 Claims, 2 Drawing Sheets

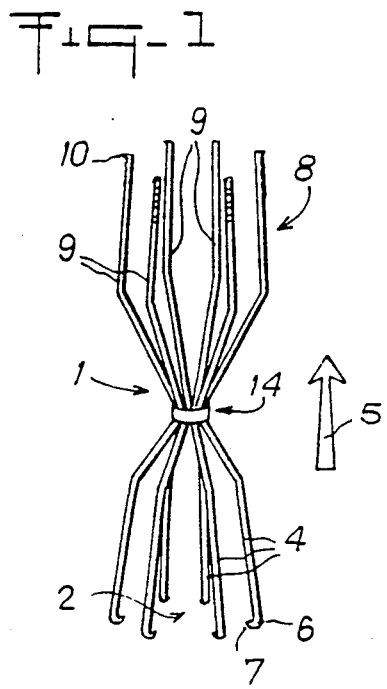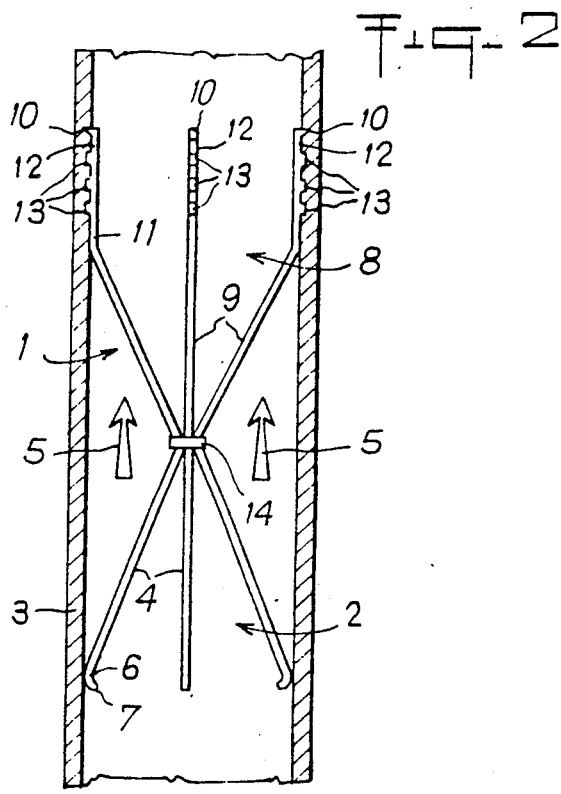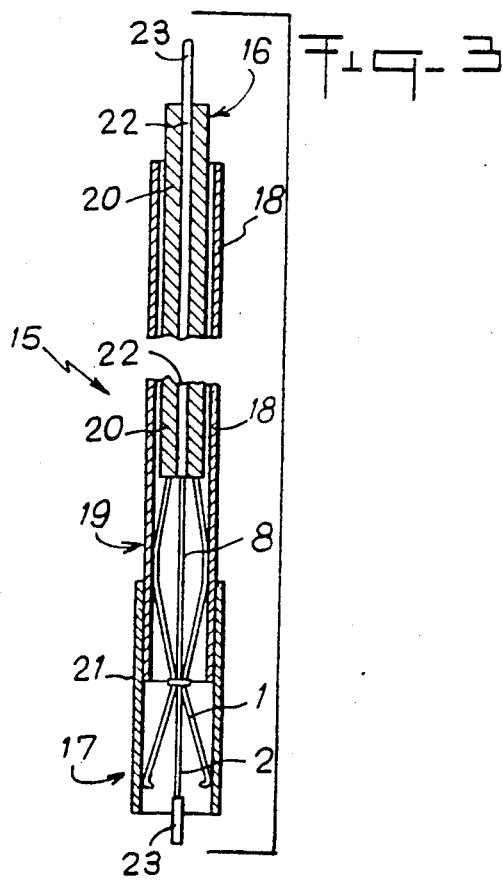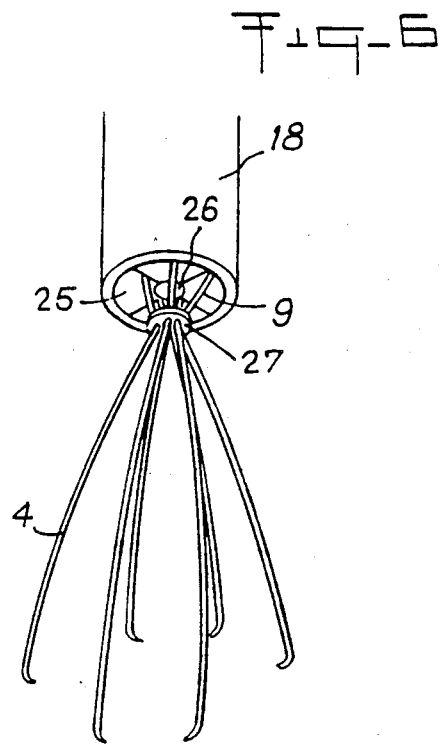

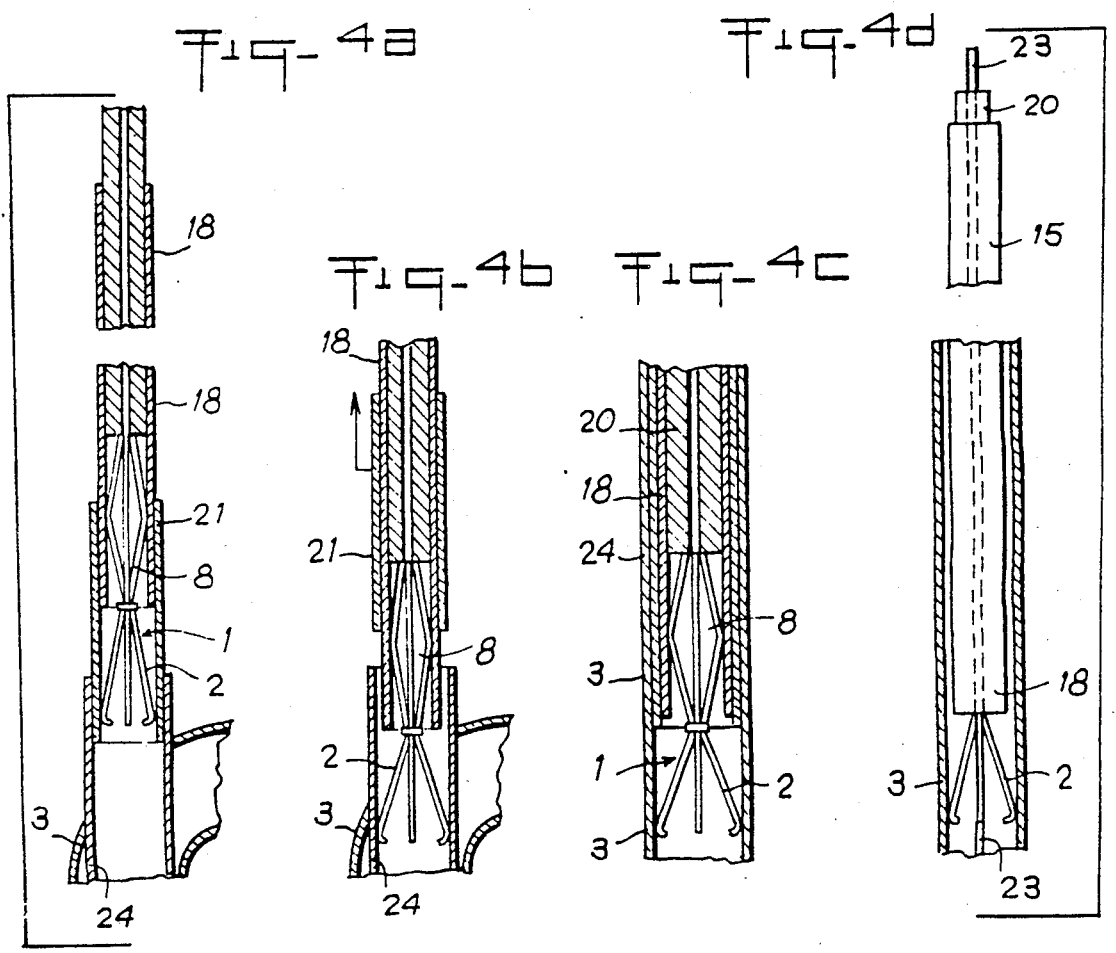
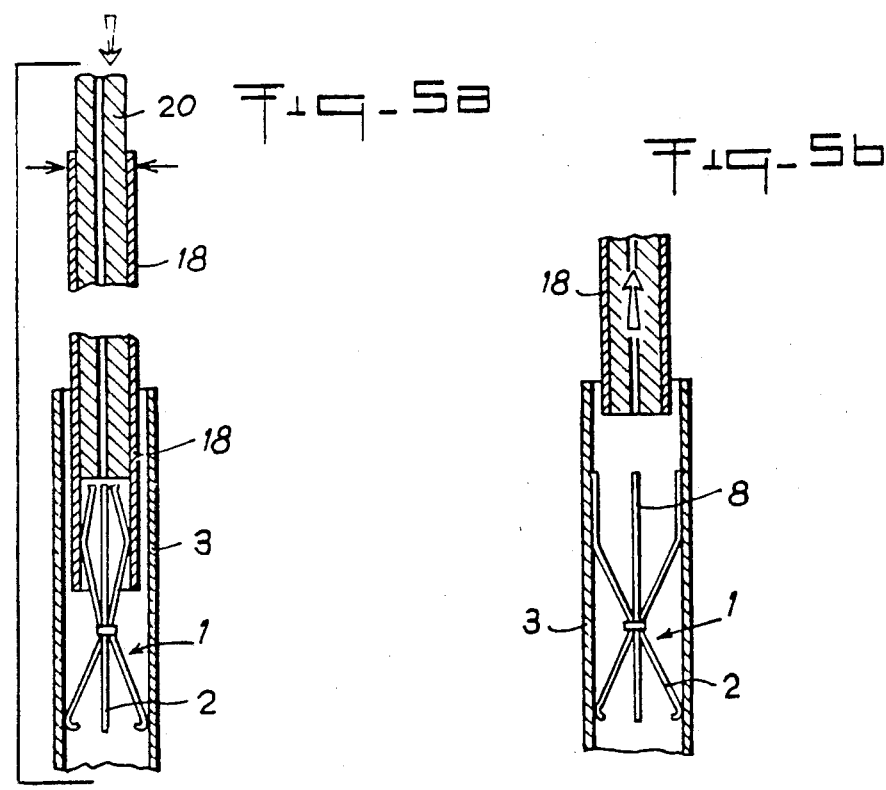

FILTER FOR MEDICAL USE

FIELD OF THE INVENTION

The present invention relates to a filter for medical use, more particularly intended to be implanted by the endovenous route, as well as to a catheter designed for positioning and using said filter.

More precisely, the filter of the present invention is a blood clot filter intended to be implanted, in certain patients, by the endovenous route, in the inferior vena cava, to prevent the migration of blood clots coming from the inferior veins of the body into the heart and pulmonary artery, in order to avoid embolism.

BACKGROUND OF THE INVENTION

Such filters are known at the present time, for example called "Greenfield filters" or "Mobin-Uddin filters" (U.S. Pat. No. 3,540,431), constituted by filiform elements disposed so as to constitute a cone permeable to the blood flow.

In order to fix the filter in the vein, the ends of the filiform elements constituting the filtration means are generally provided with hooks for anchoring, hooking in the inner wall of the vein, as described in U.S. Pat. No. 4,425,908, FR.A. No. 2 587 901 and EP.A. No. 0 270 432.

In order to implant such filters, the endovenous route is generally used; more precisely, the filter is introduced through a small vein, such as the jugular vein or the femoral vein, then the filter is guided and led towards the inferior vena cava, where it will be fixed in stable manner on opening out.

To facilitate passage, a catheter is used which, depending on the dimensions, is introduced during a surgical operation or by carrying out a method of percutaneous introduction which is less aggressive for the patient. This being so, the great majority of the existing filters are "definitive", i.e. once implanted, they can no longer be removed from the patient.

In fact, the structure of these filters is such that the means for fixing the filter, formed by anchoring hooks, hook in the inner wall of the vein, which prohibits any reverse passage.

However, certain patients present a risk of pulmonary embolism only during a brief period of time. In fact, for example, during a period of operation, or when the patients have peripheral clots, said clots may be dissolved rapidly by fibrinolytic drugs, which does not justify the definitive insertion of a clot filter.

This is why it is of interest to have available filters for the vena cava, adapted to be positioned temporarily, i.e. adapted to be left in place only for some days, for example.

In fact, in such cases, from the clinical standpoint, two possibilities exist, namely: dissolution and complete disappearance of the clots, or aggravation of the risk and persistence of the clots.

Concerning the filters for temporary use, filters similar to the definitive filters are used at the present time, although they do not bear anchoring hooks in order to allow them to be withdrawn in reverse by the endovenous route. FR. No. A.2 580 504 describes a temporary filter of this type.

In order to fix the known temporary filters, i.e. in order to avoid migration thereof in the vein, a guide is generally used, on the one hand fixed to the temporary filter and which, on the other hand, passes in the blood vessel up to the point of puncture where it is maintained in place for example by stitches.

If the evolution is satisfactory, i.e. when radiographic checks show that the state of the veins and of the vena cava has become normal and the risks of embolism have disappeared, it is advantageous to be able to remove the filter.

On the other hand, if the situation remains preoccupying and the risk of embolism remains great, it is necessary to maintain the filter in place.

Now, if a temporary filter has been used, it is then necessary to replace it by a definitive filter, which involves re-operating, either by carrying out a new operation to position another filter, or by replacing the temporary filter in place by a new definitive filter, making it necessary to reintroduce catheters and metal guides at the zone of puncture, which presents a considerable risk from the standpoint of infectious contamination.

The uncertain evolution from the clinical standpoint and the mastery of the risks of embolism being delicate, it would be of interest to have available a temporary and/or definitive filter which, after some days, may be withdrawn or be left in place definitively, without it being necessary to introduce catheters or metal guides into the patient's venous system again.

It is an object of the present invention to propose such a filter for medical use, particularly intended to be implanted in a vessel, such as the inferior vena cava, by the endovenous route, via a catheter, which overcomes the drawbacks of the known filters.

In other words, one of the objects of the present invention is to propose a filter for medical use, for temporary and/or definitive use, which may either be withdrawn without detriment to the patient's venous system, or be left definitively in place, avoiding a fresh operation which would be detrimental, taking into account the risks of infectious contamination.

Another object of the present invention is to propose a filter for medical use, adapted to be implanted by the endovenous route in the vena cava, whose definitive fixing is reinforced in order to avoid the migration of the filter during peristaltic movements.

A further object of the present invention is to propose a catheter designed for positioning and using the filter of the invention, which in particular, allows implantation thereof by the percutaneous endovenous route.

Yet another object of the present invention is to propose a catheter which controls and maintains said filter in temporary use.

In addition, said catheter of the present invention allows the introduction, upstream of the filter, of fibrinolytic product to lyse the clots which may be formed or be trapped in the filter, and in order to be able, thanks to the injection of constrast media, to check the existence of clots at the level of the filtering zone.

It is a further object of the present invention to propose a catheter which makes it possible either to withdraw the filter very easily, or to leave it in place definitively without it being necessary to re-operate.

Another object of the present invention is to propose a catheter of this type whose operation is perfectly reliable despite the risk of accumulation of fibrin.

Yet another object of the present invention is to propose a filter intended to be implanted in a vessel which, in definitive or temporary position, performs a good function of filtration, non-aggressive for the inner walls of the vessel.

Other objects and advantages of the present invention will appear in the course of the following description which has, however, only been given by way of indication and is in no way limiting.

According to the present invention, the filter for medical use, particularly intended to be implanted in a vessel such as the inferior vena cava, by the endovenous route via a catheter, said filter comprising filtering means adapted to open out in said vessel when it is positioned in the patient, is characterized in that the filtering means present no means for hooking on the wall of the vein and in that it comprises means for holding the filtering means in place with respect to the vessel, adapted to allow the passage from a situation of temporary use, i.e. being maintained for a certain period of time, the filter may be withdrawn without damage to the vessel, to a situation of definitive use, i.e. the filter may be left in place, solidly fixed on the wall of the vessel.

In addition, the catheter designed for positioning and using the filter of the invention, presenting a proximal end and a distal end, said filter, prior to being implanted in the patient, being placed at the distal end of the catheter, is characterized in that it comprises:

a down-sheath of which the distal end is adapted on the one hand to h o 1 d the filtering means non-opened out during introduction of the filter and, on the other hand, fixedly to contain the holding means during the introduction of the filter, its temporary use and its withdrawal after temporary use, a pusher, manoeuvrable from the proximal end of the catheter, adapted, for definitive use of the filter, to expel said holding means out of the down-sheath at its distal end.

It will be readily appreciated that, contrarily to what is taught in the Patents mentioned hereinabove which describe definitive filters, the filtering means must imperatively be bereft of means for hooking on the vein wall, so that, in the event of withdrawal of the filter, the filtering means may slide inside the vein without damaging it.

BRIEF DESCRIPTION OF THE DRAWINGS

The invention will be more readily understood on reading the following description with reference to the accompanying drawings, in which:

FIG. 1 illustrates an embodiment of the filter of the present invention, seen in perspective.

FIG. 2 shows the filter of FIG. 1, seen in plan view, implanted in a blood vessel.

FIG. 3 shows a view in section of a catheter according to the present invention, equipped with said filter.

FIGS. 4a to 4d show the implantation of the filter of the invention, via the catheter shown in FIG. 3, in a phase of temporary use.

FIGS. 5a and b show the passage from the situation of temporary use to the situation of definitive use of the filter of the present invention.

FIG. 6 shows a variant embodiment of a filter and of the catheter according to the present invention.

DETAILED DESCRIPTION OF THE DRAWINGS

The present invention relates to a filter for medical use, adapted to be implanted in a vessel, as well as to a catheter designed for using said filter.

The filter of the present invention will find particular application as a clot filter in the inferior vena cava in order to avoid the risks of pulmonary embolism in a patient.

From the clinical standpoint, in numerous cases, the risks are very often temporary but may persist and, in that case, the risk of embolism is very high.

As opposed to the known filters which are either temporary or definitive, the design of the filter of the present invention allows temporary and/or definitive use thereof, i.e. it may either be withdrawn after some days, or left in place definitively without an additional operation which is traumatic for the patient.

Moreover, the temporary and/or definitive filter of the present invention respects the criteria necessary in this case, namely: easy positioning by the percutaneous route, good function of filtration, good function of fixation.

Referring now to the drawings, FIGS. 1 and 2 show the filter 1 of the present invention which firstly comprises filtering means 2 adapted to open out in the blood vessel 3, particularly the inferior vena cava, when the filter is correctly positioned in the patient.

These filtering means 2 are advantageously constituted by an assembly of flexible filiform elements 4 joined together by one of their ends to form substantially the envelope of a cone, ogive or the like.

In this way, this assembly of filiform filtering elements 4 will be permeable to the blood flow, indicated by arrows 5 in the Figures, but adapted to retain the clots. To that end, it will be disposed in the direction of the blood flow, i.e. the apex of the cone or the like will be directed substantially in the same direction as the blood flow.

By way of example, the flexible rods 4 will be six in number and made of a bio-compatible material, such as a suitable metal alloy or plastics material. However, these materials will be chosen for their aptitude to elasticity and to deformation.

In fact, the rods 4 will represent a good flexibility in order, on the one hand, to be folded in a catheter of small dimensions and, on the other hand, to open out correctly in the blood vessel to form a barrage at the latter's dimensions.

Furthermore, the filiform filtering elements 4 will be such that they are non-aggressive with respect to the inner walls of the vessel.

More precisely, as shown in FIGS. 1 and 2, the rods 4 present at least a slight angle or curve 6, so that their terminal part 7 is in non-aggressive contact with the vessel, when the filtering means are opened out, but so that there is no penetration of the ends of the rods 4 in the wall of the vessel proper.

The employment of these filtering means 4 will be described in greater detail with the description of the catheter and the process for implantation of the filter described hereinbefore.

This being so, the filter 1 of the present invention, for medical use, comprises means 8 for holding in place the filtering means with respect to the vessel 3, adapted to allow the passage from a situation of temporary use of the filter 1 to a situation of definitive use thereof.

More precisely, as shown in particular in FIGS. 1 and 2, these holding means 8 are dissociated and placed downstream of said filtering means 2. They are adapted on the one hand to be folded and controlled from outside the patient to allow the filter 1 to be held for temporary use, independently of the vessel 3, and, on the other hand, after having been opened out, to allow the filter 1 to fix on the inner walls of the vessel 3 for definitive use.

More precisely, as shown by an embodiment of the present invention illustrated in FIGS. 1 and 2, said holding means 8 are constituted by an assembly of flexible filiform elements 9 joined together by one of their ends to form substantially the envelope of a cone, ogive or the like, permeable to the flow of blood 5.

The different rods 9 for fixation are made of bio-compatible material such as plastics material or suitable metal alloy. Such materials allow, for example, a good flexibility and, in addition, permit various shapes required for fixation to be made.

In particular, the ends 10 of said filiform holding elements 9 which define substantially the base of said cone or the like, are sharpened so as to be able to grip on the inner walls of the vessel 3. By way of example, FIG. 2 shows such sharpened ends 10 in the form of hooks.

In addition, in order further to increase the efficiency of the terminal parts 12, rough portions 13 will advantageously be provided, such as in particular catches, directed towards the wall of the vessel, tending to penetrate in the wall thanks to the above-mentioned pressure exerted.

The combination of these three elements, namely: sharpened ends 10, terminal part 12 and rough portions 13, will procure for the filter of the present invention a very good stability in position of definitive use and will avoid any more or less long-term migration of the filter due to the peristaltic movement of the vessel.

In the embodiment shown in the Figures, the assembly 8 of filiform holding elements 9 and the assembly 2 of filiform filtering elements 4 are disposed head-to-tail and joined by the apex of each assembly.

However, this arrangement is in no way imperative and the case may be envisaged of the two cones 2 and 8 being directed in the same direction, namely the direction imposed by the flow of blood 5, and offset with respect to each other so that the space for filtering and the space for fixing are dissociated.

Furthermore, to finish with the structure of the filter of the present invention, two other structural details may be envisaged in order to facilitate on the one hand the positioning and, on the other hand, the surgeon's work and/or to increase the efficiency of the treatment.

Concerning the latter point, the central zone of the filter, namely, in the embodiment shown in the Figures, the zone of join of the two assemblies 8 and 2 of filiform holding element 9 and of filtering elements 4, present an orifice 14 which will advantageously allow the passage of a perfusion catheter 23 adapted to convey a liquid.

In this way, via the filter of the present invention, fibrinolytic product may advantageously be introduced upstream of the filter 1, to lyse the clots which may form or be trapped by the filtering means 2.

In addition, in order to facilitate location of the clots, a contrast media may also be perfused via this catheter upstream of the zone of filtration.

Finally, in order to render use of the fixing means 8 more supple and consequently to facilitate positioning of the filter, the filiform holding elements 9 will present different lengths with respect to one another. In this way, when the filter is released, there will be a progressive opening out of the means 8 for fixing the filter 1.

This being so, in order to allow positioning and use of the filter, such as described more particularly with reference to FIGS. 1 and 2, the present invention proposes a suitable catheter.

One schematic embodiment of such a catheter is illustrated in FIG. 3. Said catheter 15 presents a proximal end 16 and a distal end 17 at the level of which said filter 1 is previously placed.

The catheter 15 comprises at least: a principal down-sheath 18, constituting the principal body of the catheter 15 whose distal end 19 is adapted on the one hand to contain said means 8 for holding the filter 1, and, on the other hand, to maintain the filtering means 2 of the filter non opened out during introduction of said filter, a pusher 20, manoeuvrable from the proximal end 16 of the catheter, adapted to expel said holding means 8 out of the down-sheath 18, at the level of its distal end 19.

In addition, in order to maintain the filtering means 2 folded, during the phase of introduction of the catheter 15, a first solution consists in integrating them in the inner distal zone 19 of the down-sheath 18.

A second solution consists in providing, at the level of the distal end 19 of the down-sheath 18, a sliding sleeve 21 adapted on the one hand to contain said folded filtering means 2 and, on the other hand, to slide on the outer sheath 18 up to the proximal end 16 of the catheter.

Finally, in order to allow the fibrinolytic product or contrast media to be released, upstream of the filter, the catheter 15 comprises a conduit 22 adapted to convey said liquid upstream of the filter.

To that end, said conduit 22 extends from the proximal end 16 to the distal end 17 coaxially to the sheath 18 and to the filter 1.

In practice, this conduit 22 is formed by a slot coaxial to the catheter inside which is introduced a complementary catheter of the multi-perforated type projecting upstream of the filter. For clarity of the drawings, this catheter 23 is shown, in FIG. 3, only at the level of the proximal zone 16 and distal zone 17.

The mode of positioning the filter of the present invention with the aid of the catheter described hereinabove is illustrated in FIGS. 4a to 4d which, in order to understand better, do not respect the relative dimensions of the different elements. Nonetheless, it should be recalled that the catheter is sufficiently fine to be able to be introduced in conventional manner by the percutaneous route.

In fact, the procedure consists in piercing the internal jugular vein, in introducing in the needle a metal guide of suitable length to descend into the inferior vena cava, then to orient, on this metal guide, a system of introduction constituted by a feed device proper (not shown in the drawings) and by its strippable sheath 24 in FIGS. 4.

When the system of introduction has been correctly positioned, below the renal veins, the metal guide and the feed device are withdrawn. On the other hand, the strippable sheath 24 is left in place.

The catheter 15 of the present invention is then introduced into the strippable sheath 24, as shown more particularly in FIG. 4a.

The filter 1 is arranged in completely folded position in the down-sheath 18, the holding means 8 being folded inside the distal end 19 of the sheath 18, and the filtering means 2 being outside the distal part 19 of the sheath but maintained folded by the sliding sleeve 21, projecting for the moment with respect to the distal end of the sheath 18.

Furthermore, the perfusion catheter 22, 23 (not shown in the Figure in order not to overload it) descends inside said catheter 15 as far as the interior of the filter 1.

FIG. 4b shows the following phase of the introduction of the catheter 15, and in particular shows the introduction of the filtering means 2 in the strippable sheath 24.

Once the filtering means 2 are completely introduced into the strippable sheath 24, the sleeve 21 may be slid on the sheath so that the means 2 then opening out of said sheath 18, are maintained folded by the strippable sheath 24.

FIG. 4c shows the issue of the phase of introduction of the catheter 15, i.e. substantially the coming into register of the distal part of the down-sheath 18 and the distal part of the strippable sheath 24.

At that level, the filter, or more precisely the filtering means 2 of the filter emerge from the strippable sheath 24, open out, and perform their function of filtration.

The strippable sheath 24 may then be withdrawn, particularly by tearing, the filter then being in temporary position as shown in FIG. 4d, the filtering means 2 being opened out and the holding means 8 folded in the sheath 18.

During this phase of temporary use, the perfusion catheter 23 may advantageously be used either for diffusing, upstream of the filter, an opaque product for checking the existence of clots at the level of the filtering zone 8, or for perfusing fibrinolytic products to lyse the clots trapped in this zone.

In this phase of use, the filter is maintained in place by the catheter 15 thanks to the holding means 8 which are folded in the inner distal end 19 of the down-sheath 18, the friction between these two elements being such that the filter, and consequently the holding means, cannot escape from the catheter. In other words, the down-sheath 18 is made of a material such that the coefficient of friction between the holding means and the sheath is greater than the coefficient of friction between the filtering means 2 and the blood vessel 3.

This being so, in this so-called temporary phase, in order to allow the filtering means 2 to be maintained in place with respect to the vessel 3, the catheter 15 will advantageously be fixed in accordance with conventional methods at the point of puncture, for example by stitches in the muscle or any suitable means.

After the monitoring phase, during which the surgeon monitors the evolution from the clinical standpoint, he is faced with two possibilities, either the withdrawal of the filter or the definitive implantation thereof.

If the surgeon decides to withdraw the filter, it then suffices to eliminate the cutaneous fixation, particularly by cutting the stitches, and to raise the whole in order to bring out the filter and the filtering means via the puncture orifice.

On the contrary, if the clinical situation remains preoccupying and the risks of embolism remain high, it will be necessary to leave the filter 1 in place definitively.

FIGS. 5a and 5b show this procedure by which the filter 1 is ejected from the sheath 18 of the catheter 15.

More precisely, the fixing means 8 are brought into projection with respect to the sheath 18 by a relative movement of the pusher 20 with respect to the sheath 18.

A manoeuvre, using the pusher as a stop on raising the sheath in order to release the filter, in the manner of a glove finger, represents the manoeuvre most adapted to leave the filter in the position decided previously. Nevertheless, other arrangements may be adopted.

In this way, the pusher 20 makes it possible definitively to eject the filter from the sheath and the flexible elements 9 of the fixing means 8, due to their different sizes, and when the sheath is withdrawn, to release them progressively for a more precise hooking.

FIG. 5b illustrates the definitive positioning of the filters and the withdrawal of the sheath 18 of the catheter 15.

In certain cases, in particular in the case of prolonged temporary use, an accumulation of fibrin may occur inside the catheter around the filiform holding elements 9, with the result that, upon expulsion of the filter, these filiform elements 9 risk being blocked in folded position and not opening out perfectly.

In order to overcome this drawback, the catheter or at least the distal end of the sheath 18 presents, longitudinally, independent housings 25, in each of which a filiform element 9 is threaded during positioning of the filter on the catheter. FIG. 6 shows a filter according to the invention of which the filtering means are composed of six filiform elements 4 and the holding means of four filiform elements 9; each filiform holding element 9 is positioned in its housing 25; the distal end of the sheath 18 further comprises a fifth cylindrical and axial housing 26. This housing 26 allows passage of the pusher between the four housings 25 and therefore the filiform holding elements 9; when the filter is released, the pusher abuts on the rivet 27 ensuring join between the filtering elements and the holding elements.

This particular embodiment of the catheter presents as complementary advantage that of avoiding the entangling of these filiform holding elements 9 which was sometimes observed when they were placed all together in the catheter, without compartmentation.

Other embodiments of the present invention, within the scope of the man skilled in the art, may, of course, be envisaged without departing from the scope thereof.

What is claimed is:

1. A medical filter adapted to be implanted in a blood vessel of a patient through the endovenous route via a catheter, said blood vessel having a flow of blood therethrough and possible clots and an inner wall, said filter comprising filtering means adapted to open out in said vessel when positioned within the patient,
said filtering means being formed without hooking means for engaging the inner wall of said vessel,
and means for holding said filtering means in place with respect to the vessel,
said holding means permitting temporary use of said filter and passage from a situation of temporary use wherein the filter may be withdrawn from the vessel to a situation of definitive use of the filter.

2. The filter of claim 1 wherein said holding means are located downstream from said filtering means and are constructed and arranged to be connected and monitored from outside the patient to allow the filter to be held for temporary use independently of the vessel or to be opened out to allow the filter to fix on the inner wall of the vessel for definitive use.

3. The filter of claim 1 wherein said holding means comprises an assembly of flexible filiform elements, said elements having first ends and means for joining said first ends, said elements lying in the surface of a solid geometric figure such as a cone or ogive or the like amd being permeable to said flow of blood.

4. The filter of claim 3, wherein said filiform holding elements present different lengths with respect to one another.

5. The filter of claim 3 wherein said elements have second ends, said second ends being sharpened.

6. The filter of claim 3 wherein said elements have terminal holding parts, said terminal parts having rough portions for engaging said inner wall of said vessel to avoid migration of the filter when used definitively.

7. The filter of claim 1 whereinsaid filtering means comprises an assembly of flexible filiform elements, said elements having first ends, and means for joining said first ends, said elements lying in the surface of a solid geometric figure such as a cone or ogive or the like oriented in the direction of said blood flow and permeable to the flow of blood while retaining said clots.

8. The filter of claim 7 in which said elements have terminal parts remote from said first ends, said filiform filtering elements presenting at least a slight angle or curve such that said terminal parts are in contact in non-aggressive manner with the inner wall of the vessel in the temporary or definitive use position of the filter.

9. The filter of claim 3 wherein the filtering means comprises an assembly of flexible filiform elements having first ends and means for joining said ends, said filtering elements lying in the surface of a solid geometric figure such as a cone or ogive or the like oriented in the direction of blood flow permeable to blood flow but adapted to retain such clots, each of said filtering filiform and holding filiform assemblies has a head and a tail and an apex, said filtering and holding assemblies being disposed in head-to-tail relationship and being joined at said apices.

10. The filter of claim 9 wherein the joined apices of said assemblies forms an orifice.

11. A catheter for positioning and using a filter which is to be implanted in the blood vessel of a patient, said filter having filtering means adapted to open out from a folded condition in the vessel of the patient when positioned therein and holding means, said catheter presenting a proximal end and a distal end in which said filter is placed prior to implantation in the patient, said catheter comprising a down-sheath, the distal end of which holds the filtering means non-opened out during the introduction of the filter and fixedly to contain the holding means during introduction and temporary use and withdrawal of the filter after temporary use and a pusher maneuverable from the proximal end of the catheter for expelling the holding means out of the down-sheath at its distal end in the case of definitive use of the filter.

12. The catheter of claim 11, said catheter passing into the blood vessel through a previously placed strippable sheath of introduction, said catheter comprising a sliding sleeve at the distal end of said down-sheath for containing said folded filtering means and slidable up toward the proximal end of said down-sheath whereby said filtering means projects from said down-sheath while being maintained folded in said strippable sheath for introduction.

13. The catheter of claim 11, wherein it comprises a conduit adapted to convey a liquid upstream of said filter, said conduit extending from the proximal end to the distal end of the catheter coaxially to the down-sheath and to the filter.

14. The catheter of claim 11, whereby the down-sheath is made of a material such that the coefficient of friction between the down-sheath and the holding means is greater than the coefficient of friction between the filtering means and the blood vessel.

15. The catheter of claim 11, in which the filter holding means comprises a plurality of filiform elements, said distal end of said down-sheath being longitudinally compratmented into a plurality of independent housings for receiving the respective elements.

16. The catheter of claim 15, wherein the down-sheath or its distal end comprises a central housing in which may slide the pusher for expulsion of the filter.

* * * * *